United States Patent [19]
Shillington et al.

[11] Patent Number: 5,323,994
[45] Date of Patent: Jun. 28, 1994

[54] MOUNTING BRACKET FOR MOUNTING A SECOND CONTAINER TO A FIRST CONTAINER BRACKET

[75] Inventors: Richard A. Shillington, Leucadia; Gilbert Packer, Carlsbad; Rex O. Bare, Lake Forest; David R. Millar, Irvine, all of Calif.

[73] Assignee: Med-Safe Systems, Inc., Oceanside, Calif.

[21] Appl. No.: 973,849

[22] Filed: Nov. 9, 1992

[51] Int. Cl.⁵ .............................................. A47B 96/00
[52] U.S. Cl. ...................................... 248/229; 211/13
[58] Field of Search ............... 248/220.2, 221.3, 223.4, 248/231.8, 229; 211/13

[56] References Cited

U.S. PATENT DOCUMENTS

| | | | |
|---|---|---|---|
| 2,879,018 | 3/1954 | Pence | 248/220.2 |
| 2,914,288 | 11/1959 | Beller | 248/229 X |
| 2,982,509 | 5/1961 | Murray | 248/229 |
| 5,040,712 | 8/1991 | Pesonen et al. | 248/220.2 |
| 5,103,997 | 4/1992 | Shillington et al. | 220/481 |

Primary Examiner—Alvin C. Chin-Shue
Assistant Examiner—Sarah A. Lechok
Attorney, Agent, or Firm—Baker, Maxham, Jester & Meador

[57] ABSTRACT

A mounting bracket assembly for mounting a second container to a first container bracket comprises a first mounting bracket for mounting to a vertical wall for mounting a first container, the bracket having a vertical panel portion with an upper horizontal edge and lower horizontal edge, a second mounting bracket having a vertical arm with a hook at an upper end arm for latching engagement with the upper horizontal edge, and a latching arm extending outward from a lower end of the vertical arm for latching engagement with and supporting a second housing.

19 Claims, 3 Drawing Sheets

५,३२३,९९४

MOUNTING BRACKET FOR MOUNTING A SECOND CONTAINER TO A FIRST CONTAINER BRACKET

BACKGROUND OF THE INVENTION

The present invention relates to the mounting of disposable containers for hospital sharps and dispensing containers for hospital supplies, and pertains particularly to a mounting bracket assembly for mounting a supply container to a mounting bracket of a disposable container.

Hospitals and medical clinics use great quantities of sharps, such as needles, syringes, surgical blades, and the like, that are disposed of rather than cleaned and reused. It is necessary that the sharps be disposed of in a manner that prevents them being reused without sterilization. In particular, it is necessary to keep them from falling into the hands of those, such as intravenous drug users and the like, who are likely to use them without proper sterilization.

Numerous containers have been developed in recent years, which are reasonably secure and disposable for receiving and disposing of hospital sharps, wastes and the like. Many of these disposable containers, however, are out dated and do not provide adequate security against pilfering of used syringes and the like from such containers. While improved containers have been developed which cannot readily be reopened and articles cannot be easily removed therefrom, such containers must be kept in a secure place or securely mounted to non-removable structure to prevent unauthorized removal. The disposable container and its mounting bracket must not only be secure, it must be simple and inexpensive to manufacture, and it must be simple and easy to use and to mount and remove the container.

Reasonably secure mounting brackets have been developed and are widely used to prevent unauthorized removal of the containers. However, more recently developed improved containers have new and improved mounting brackets which are easier to mount and use and are more secure. These brackets are typically mounted on walls or similar surfaces and are securely anchored by lag bolts and the like.

An example of a recently developed improved container and mounting bracket is disclosed in U.S. Pat. No. 5,103,997, granted Apr. 14, 1992 to Shillington et al. This patent discloses a sharps container having a mounting bracket adapted to be mounted to a wall with interengaging projections and slots on the bracket and container, and a locking lever for securing the container to the bracket.

There is always a need for convenient placement and mounting of other containers, such as supply containers. In most examining and operating rooms, there already exists a number of containers conveniently mounted to walls and other support structure.

It is, therefore, desirable that an improved bracket assembly be available for mounting a second container to a bracket of a first container.

SUMMARY AND OBJECTS OF THE INVENTION

It is the primary object of the present invention to provide an improved bracket assembly for mounting containers.

In accordance with a primary aspect of the present invention, a mounting bracket assembly comprises a pair of L-shaped brackets for detachably mounting a second container to a support bracket of a first container.

BRIEF DESCRIPTION OF THE DRAWING

The above and other objects and advantages of the present invention will become apparent from the following description when read in conjunction with the accompanying drawings wherein.

DETAILED DESCRIPTION OF A PREFERRED EMBODIMENT

Figure 1:
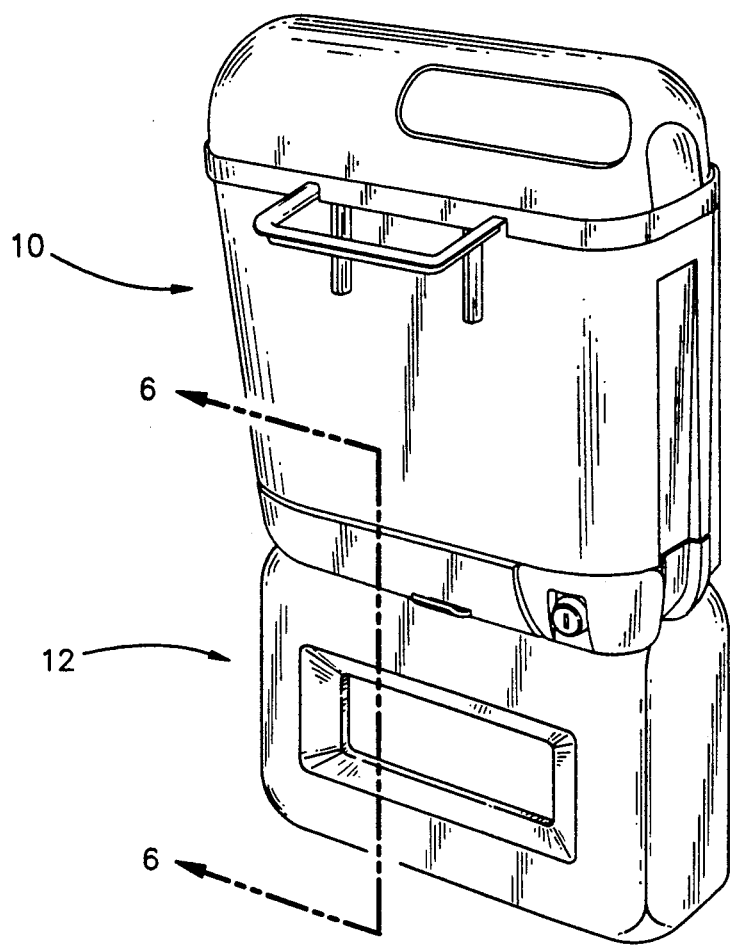
FIG. 1 is a perspective view of a pair of containers mounted in accordance with an exemplary embodiment of the invention.

Referring to FIG. 1 of the drawing, there is illustrated an exemplary embodiment of a disposable sharps container 10 below which is mounted to a second container, such as a glove dispenser 12. The disposable container comprises a generally rectangular box-like housing, formed of the usual plastic material for such containers, and detachably mounted to a primary wall bracket that is attachable to a vertical wall. The container 12 is mounted below the disposable container by means of a second bracket assembly that mounts directly to the disposable container primary bracket. This eliminates the need for putting additional holes and lag bolts in the wall.

Figure 2:
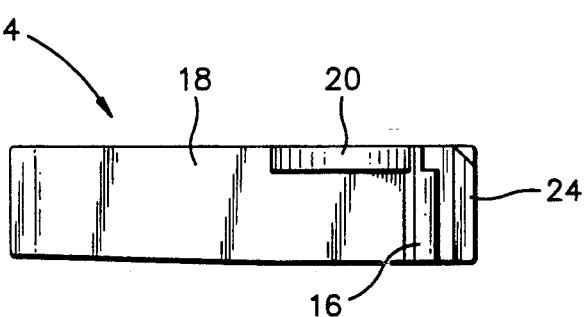
FIG. 2 is a top plan view of a mounting bracket in accordance with a preferred embodiment of the invention.
Figure 3:
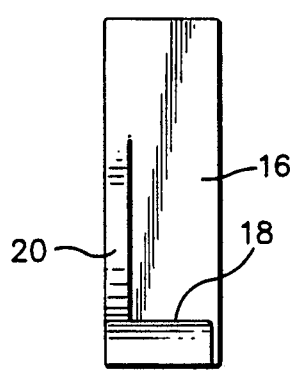
FIG. 3 is a front elevation view of the bracket of FIG. 2.
Figure 4:
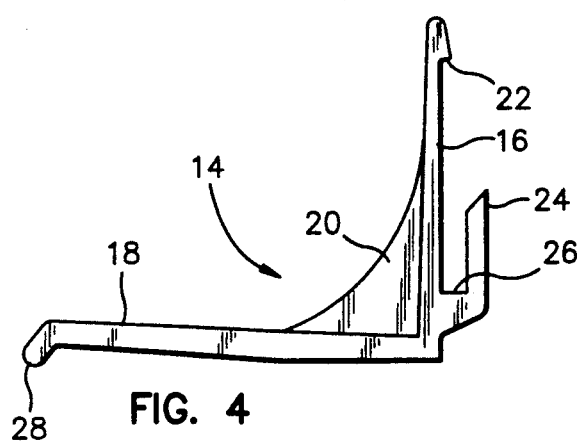
FIG. 4 is a side elevation view of the mounting bracket of FIG. 2.
Figure 5:
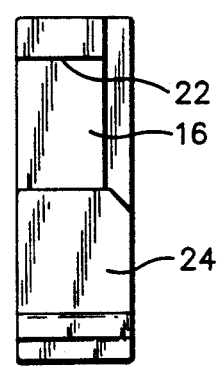
FIG. 5 is a back elevation view of the bracket of FIG. 2.

Referring to FIG. 2, an exemplary embodiment of a mounting bracket in accordance with the present invention is illustrated. The mounting bracket comprises a generally L-shaped member having a vertical arm 16 and a horizontal arm 18 joined at a right angle to one another. The arms have a generally rectangular cross section and with a web or brace member 20 positioned at one side of the juncture extending partially along both arms. The brace member 20 has a generally triangular configuration.

The vertical arm 16 has a latch dog or shoulder 22 at the upper end for latching over a horizontal edge of a vertical panel of a wall bracket. A finger 24 is spaced from and extends parallel to the arm to engage the opposite side of a vertical panel. A shoulder 26 formed by a connection between the arm and finger may engage a lower edge of the panel. The horizontal arm 18 has an outer end with a tip 19 that is sloped downward. The terms vertical and horizontal are used herein to identify the arms in their normal position when in use.

Figure 9:
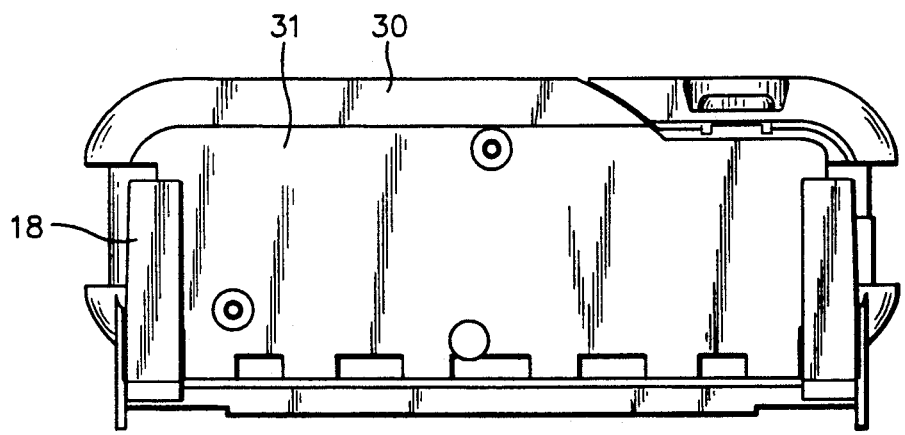
FIG. 9 is a bottom view from below of a lower part of the primary mounting bracket.
Figure 10:
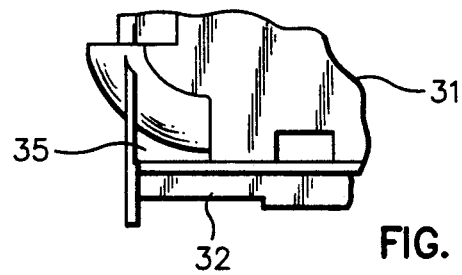
FIG. 10 is an enlarged detailed view of a lower part of the primary mounting bracket showing an opening for the second bracket.

The bracket member, as illustrated and described with respect to FIGS. 2-5 (hereinafter sometimes referred to as a second or auxiliary bracket), comes in pairs with a left unit and a right unit, and are designed to fit the mounting brackets (sometimes called primary bracket) as disclosed and covered in U.S. Pat. No. 5,103,997, issued Apr. 14, 1992, to Shillington et al of common assignment herewith, and incorporated herein by reference as though fully set forth. The disposable container mounting bracket, as can best be seen in FIG. 6, comprises a vertical panel 28 for mounting to a wall. The panel is attached to a lower lock housing 30 having a bottom wall 31, and which contains a latch and lock mechanism for releasably locking the disposable container 10 to the overall mounting bracket. The housing 30 is attached to the vertical wall panel by means (not shown) which leaves vertical passages between a portion of the lock housing and vertical wall panel as can be seen in FIGS. 9 and 10.

Figure 7:
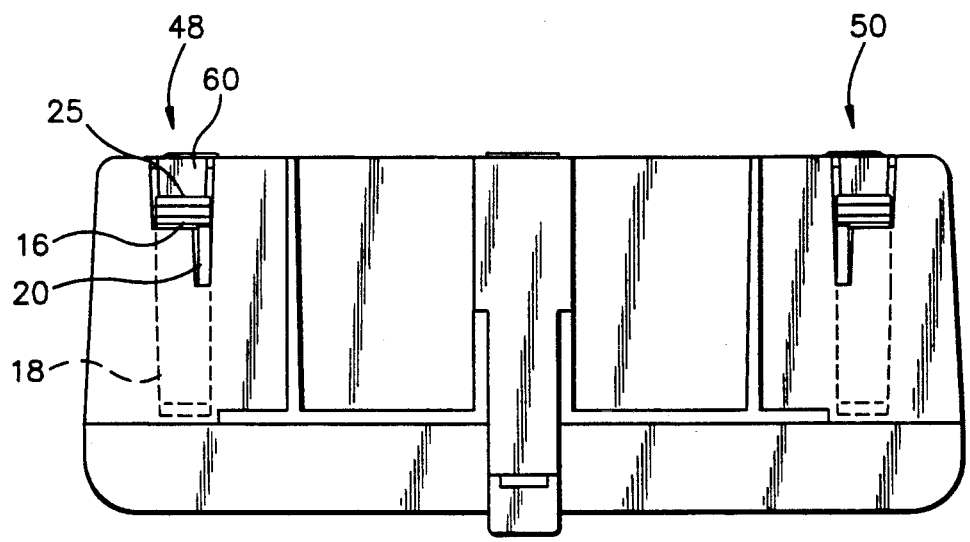
FIG. 7 is a top plan view of the second container of FIG. 6.

The lower edge portion of the wall panel 28 includes a vertical panel portion 32 having an upper horizontal edge 34 and a lower horizontal edge 36. The vertical arm 16 of the bracket 14, as shown in FIG. 7, is designed to extend along a passage between the vertical panel portion 32 and the lock housing portion 30 so that latch 22 latches over ledge 34, with finger 24 extending behind panel 32 and retaining the finger 16 against the opposite face thereof. The web 20 is curved to accommodate the curvature of the lock housing 30.

The elongated horizontally extending arm 18 of the attachment bracket is adapted to extend into a slot in the top of a housing or container and to retain the container in place beneath the container 10.

Figure 6:
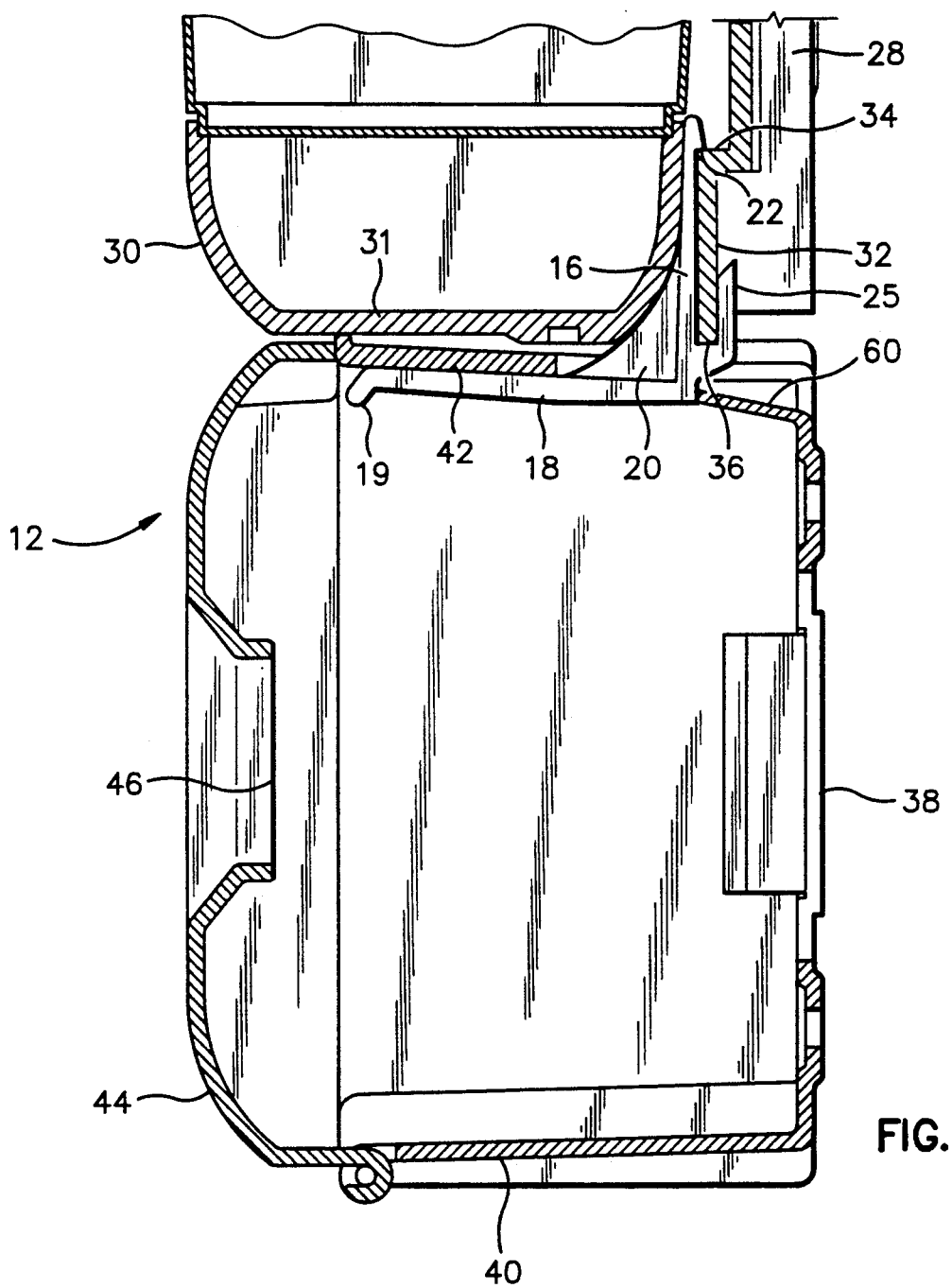
FIG. 6 is a section view taken on line 6—6 of FIG. 1.
Figure 8:
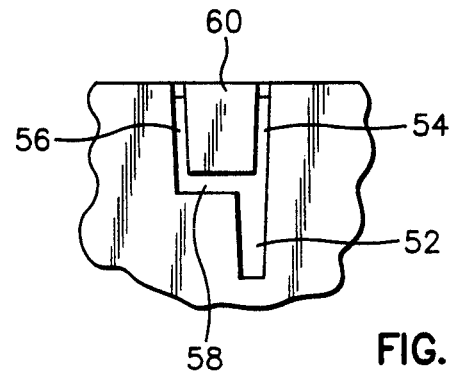
FIG. 8 is an enlarged detailed view of a bracket engaging slot.

The container 12 in the illustrated embodiment (FIGS. 6 and 7) is designed as a glove dispenser for use by medical personnel. The container comprises a generally box-like housing having a back wall 38, bottom wall 40, top wall 42 and a front wall 44. The front wall or panel includes an opening 46 through which gloves are dispensed. The top wall 42 is provided with a pair of spaced apart bracket latching slots, designated generally at 48 and 50, as been seen in FIG. 8. These latching slots each have a generally "h" configuration, with an elongated slot 52 having a lower leg portion 54 cooperating with an adjacent parallel leg portion 56, and a transverse portion 58 forming a latch tab 60, which engages the back lower edge of arm 16 of the bracket, as shown in FIG. 6, for latching the bracket in place. The web portion of the bracket extends into slot 52 and adds additional strength and stability to the assembly.

The lower or horizontal leg 18 of the bracket extends into the slot area over tab 60 and slides forward beneath the top or upper wall 42 of the container until the lower back edge of the arm 16 passes forward of the forward edge of tab 60 so that it snaps up into engagement to retain the housing into a latched position as shown in FIG. 6. The arm 18 preferably biases the top 42 of the container 12 into engagement with bottom 31 of lock housing 30 to enhance the stability thereof.

In operation, when it is desired to mount a container, such as 12 to a bracket of a first or disposable container such as 10, a pair of the brackets 14 are selected and inserted upward into the outermost spaces or holes (one shown 35) between the latch housing 30 and vertical panel 32 of the mounting bracket panel 28 (FIGS. 9 and 10). The latching hook or shoulder 22 of arm 16 latches over the upper edge 32 as finger 25 extends behind panel 32 to retain it in position and stabilize the bracket (FIG. 6). Once the two brackets are in position, a container 12 is selected and positioned such that the outermost tip 19 of the arm 18 extends downward over and forward of a latch tab 60 beneath the upper wall 42 of the container. As the container is forced backward, the leg or arm 18 extends forward beneath the upper wall 42 as it moves backward to a position to enable latch 60 to pop up and latch behind in the arm 16 at the back corner of the bracket. Thus, the dispensing container is latched in place beneath the disposable container.

While we have illustrated and described our invention by means of specific embodiments, it is to be understood that numerous changes and modifications may be made therein without departing from the spirit and scope of the invention as defined in the appended claims.

We claim:

1. A mounting bracket assembly for mounting a second container to a first container bracket, comprising:
   a first mounting bracket for mounting to a vertical wall for mounting a first container, said first mounting bracket having a vertical panel portion with an upper horizontal edge and lower horizontal edge, said upper edge being vertically spaced above said lower edge;
   a second mounting bracket having a vertical arm for extending along one surface of said panel portion and hook means at an upper end of said vertical arm for latching engagement with said upper horizontal edge;
   a finger extending parallel to said vertical arm for extending along an opposite surface of said vertical panel portion for biasing said vertical arm toward said one surface thereof; and
   latching means extending outward from a lower end of said vertical arm for latching engagement with and supporting a second housing.

2. A mounting bracket according to claim 1 wherein said latching means comprises an elongated horizontal arm extending outward for extending into a slot in a top of a second housing.

3. A mounting bracket according to claim 2 wherein said vertical arm and said horizontal arm have a rectangular cross section along a majority of the length thereof.

4. A mounting bracket according to claim 3 wherein said vertical arm and said horizontal arm are connected at a right angle juncture and have a web at a side of said juncture.

5. A mounting bracket according to claim 4 wherein said second container comprises a generally box-like enclosed container having a top having a slot for receiving said horizontal arm and a latch tab in said slot for latchably engaging said second bracket.

6. A mounting bracket according to claim 1 wherein:
   said latching means extending outward from a lower end of said vertical arm comprises an elongated horizontal arm for engagement with a slot in a top of a second container;
   said second container comprises a box-like housing having a top wall and a slot in said wall for receiving said horizontal arm and forming a latch tab for engaging a surface of said vertical arm.

7. A mounting bracket according to claim 6 wherein said slot has an h configuration with portions of said slot forming a latching tab.

8. A mounting bracket according to claim 1 wherein said first mounting bracket comprises a latch housing at the bottom of said panel; and said vertical arm extends through an opening between said panel and said housing.

9. A mounting bracket according to claim 8 wherein:

said latching means extending outward from a lower end of said vertical arm comprises an elongated horizontal arm for engagement with a slot in a top of a second container;

said second container comprises a box-like housing having a top wall and a slot in said wall for receiving said horizontal arm and forming a latch tab for engaging a surface of said vertical arm.

10. A mounting bracket according to claim 9 wherein said slot has an h configuration with portions of said slot forming said latching tab.

11. A mounting bracket assembly for mounting a second container to a first mounting bracket of the type for mounting to a vertical wall for mounting a first container, said first mounting bracket having a vertical panel portion with an upper horizontal edge and lower horizontal edge, said upper edge being vertically spaced above said lower edge, comprising:

a second mounting bracket having a vertical arm for extending along one surface of said panel portion and hook means at an upper end of said vertical arm for latching engagement with said upper horizontal edge;

a finger extending parallel to said vertical arm for extending along an opposite surface of said vertical panel portion for biasing said vertical arm toward said one surface thereof; and latching arm means extending outward from a lower end of said vertical arm for latching engagement with and supporting a second container.

12. A mounting bracket according to claim 11 wherein said second container comprises a generally box-like enclosed container having a top having a slot for receiving said latching arm means and a latch tab in said slot for latchably engaging a surface of said vertical arm.

13. A mounting bracket according to claim 12 wherein said latching arm means comprises an elongated horizontal arm, said vertical arm and said horizontal arm connected at a right angle juncture and have a web at a side of said juncture.

14. A mounting bracket according to claim 13 wherein said slot has an h configuration with a portion of said slot accommodating said web.

15. A mounting bracket according to claim 14 wherein said tab is formed by parallel portions of said slot.

16. A mounting bracket assembly for mounting a second container to a first mounting bracket of the type for mounting to a vertical wall for mounting a first container, said first mounting bracket having a vertical panel portion with an upper horizontal edge and lower horizontal edge, said upper edge being vertically spaced above said lower edge, comprising:

a generally box-like enclosed container having a top with bracket attachment means including a pair of spaced apart slots;

a pair of generally L-shaped mounting brackets, each having a vertical arm for extending along one surface of said panel portion and hook means at an upper end of said vertical arm for latching engagement with said upper horizontal edge;

a finger extending parallel to said vertical arm for extending along an opposite surface of said vertical panel portion for biasing said vertical arm toward said one surface thereof; and an elongated latching arm extending outward from a lower end of said vertical arm for latching engagement with said spaced apart slots.

17. A secure mounting bracket according to claim 16 wherein said spaced apart slots have an h configuration with portions of said slot forming a latch tab.

18. A mounting bracket according to claim 17 wherein said vertical arm and said latching arm have a rectangular cross section along a majority of the length thereof.

19. A mounting bracket according to claim 18 wherein said vertical arm and said latching arm are connected at a right angle juncture and have a web at a side of said juncture.

* * * * *